United States Patent [19]

Morrison

[11] 3,987,795
[45] Oct. 26, 1976

[54] ELECTROSURGICAL DEVICES HAVING SESQUIPOLAR ELECTRODE STRUCTURES INCORPORATED THEREIN

[75] Inventor: Charles F. Morrison, Boulder, Colo.

[73] Assignee: Valleylab, Inc., Boulder, Colo.

[22] Filed: Aug. 28, 1974

[21] Appl. No.: 501,224

[52] U.S. Cl. .................. 128/303.14; 128/303.17
[51] Int. Cl.$^2$ .................. A61B 17/32; A61N 3/06
[58] Field of Search ............... 128/303.14, 303.15, 128/303.16, 303.17, 303.13, 404, 405, 407–409

[56] References Cited

UNITED STATES PATENTS

| | | | |
|---|---|---|---|
| 452,220 | 5/1891 | Gunning | 128/408 |
| 1,814,791 | 7/1931 | Ende | 128/303.17 |
| 1,916,722 | 7/1933 | Ende | 128/303.17 |
| 1,983,669 | 11/1934 | Kimble | 128/303.17 |
| 2,275,167 | 3/1942 | Bierman | 128/303.17 |
| 3,858,586 | 1/1975 | Lessen | 128/303.17 |
| 3,920,021 | 11/1975 | Hildebrandt | 128/303.17 |

Primary Examiner—Robert W. Michell
Assistant Examiner—Lee S. Cohen
Attorney, Agent, or Firm—Gerald J. Ferguson, Jr.; Joseph J. Baker

[57] ABSTRACT

An electrosurgical device connected to an electrical generator having active and return output terminals, the device being used to cut, coagulate, or otherwise treat human tissue or the like, the device comprising: an electrode support; an active electrode responsive to the active output terminal and a return electrode responsive to the return output terminal, the electrodes being supported by the electrode support, both the electrodes being adapted for electrical connection to the tissue, the ratio of the return electrode area adapted to electrically connect to the tissue to the active electrode area adapted to ohmically or arc-wise connect to the tissue being in the range of approximately 2 to 200. Arrangements are also provided for separating the active electrode from the tissue when the device is placed in contact with the tissue to insure that a current arc is established between the active electrode and the tissue. Various electrode configurations are also disclosed.

8 Claims, 41 Drawing Figures

ELECTROSURGICAL DEVICES HAVING SESQUIPOLAR ELECTRODE STRUCTURES INCORPORATED THEREIN

BACKGROUND OF THE INVENTION

This invention relates to electrosurgical devices and in particular to such devices having sesquipolar electrode structures incorporated therein.

In conventional monopolar electrosurgery, radio frequency (RF) power of various wave forms and amplitudes is applied to the body of a patient with a very small area active electrode such that a localized interaction produces cutting, coagulation, fulguration, or desiccation. The return path for the RF current is via a large area return electrode so that interaction at this interface is insignificant.

In conventional bipolar electrosurgery, a pair of electrodes are close together, small and essentially identical so that significant and equal interactions occur with the body at both surfaces. When attempting to make electrosurgery more simple and more safe, one is drawn to the bipolar mode. No lasting electrical connections ar made to the patient, it is all in the hand of the surgeon. Further, bipolar devices, especially when used with RF sources that are isolated from ground, significantly reduce the danger of RF burns at intentional and at inadvertent ground connections to the patient. Also, possible dangers from passage of large RF currents through the body are eliminated, and the interaction of the RF with other instrumentation is minimized. The convenience and added safety of not having a large, separately placed return electrode are also significant.

A number of bipolar devices have been proposed and produced. The most commonly used bipolar electrode devices appear to be the tips of forceps (current passes from tip to tip through the grasped flesh), and dual needles. For many years, minor coagulation and desiccation, especially is cosmetic and neurosurgery have been performed in the bipolar mode. However, bipolar technology has not proved to be a satisfactory substitute for conventional monopolar electrosurgery in most applications, especially those requiring cutting and heavy coagulation. The most fundamental difficulty is that biactive electrodes require an equal voltage drop at each of the electrodes. When arcing is required as for cutting or heavy coagulation, this taxes the output capability of the available generators. Modification of the generator or to produce such high voltages results in a problem of extraneous arcs at the electrodes. However, a more important problem is that, when sufficient voltage for correct bipolar arcing operation is present, conditions for starting to cut are too violent for any but the most crude surgical techniques. If one electrode touches the flesh before the other when starting to cut, the initial arc at the second electrode is unduly destructive. Thus, there are obvious safety and convenience advantages associated with bipolar devices, and yet there is a lack of available equipment for obtaining these advantages for most applications such as cutting or heavy coagulation.

For the purposes of the present invention, "sesquipolar" sesqui from the Latin for 1-½times) electrode devices are utilized. In such devices, the area of the return electrode is substantially smaller than that of monopolar devices. The term "sesquipolar" has been defined for purposes of this invention and the definition thereof will be further elaborated hereinafter. The active and return electrodes of a sesquipolar device may both be in the operational site, as with bipolar devices, but only one of them is intentionally highly interactive. Because the return electrode is rather small, there is some interaction, making it intermediate between conventional mono and bipolar modes of electrosurgery.

The sesquipolar return electrode is not merely a scaled down return electrode of the more conventional monopolar technology. Any decrease in the size of the conventional monopolar return electrode (even though an order of magnitude away from the sesquipolar device of this invention is rejected by the safety committees and standards groups). Indeed, in monopolar electrosurgery the avoidance of any detectable interaction at the return electrode (which is allowable in the sesquipolar mode) is fundamental. Otherwise burns obtained at nonsurgical sites can result in disfiguration and concomitant suffering. In fact, burns are occasionally obtained at small area inadvertent connections to ground, and at improperly administered return electrodes. Sesquipolar technology, in contrast, may be viewed as bipolar from the safety point of view, and return electrode area will not be a matter of concern from a safety point of view. And yet, there are very clear-cut distinctions from conventional bipolar systems. For example, bipolar technology has carefully respected symmetry, insisting categorically that both electrodes be equally active.

Sesquipolar devices provide the advantages of both the bipolar and the monopolar devices, while larlely eliminating the technical difficulties of the bipolar and the dangers associated with conventional monopolar electrosurgical devices. For example, since the less active electrodes of sesquipolar devices operates with significantly reduced voltage drop, the output of conventional electrosurgical generators is sufficient to drive this type of electrode system in major operations. There is no problem of control in delicate surgery.

There has been disclosed in U.S. Pats. Nos. 2,004,559; 2,002,594; and 2,056,377 electrosurgical tools wherein the ratio of the area of the active electrode to the return electrode may be small although there is not explicit teaching of this in the above patents. Further, the active and return electrodes in the above patents are relatively pivotally mounted with respect to one another and thus the electrosurgical tools described therein are essentially limited to the cutting of flat surfaces and thus unduly limited for general surgical purposes.

OBJECTS OF THE INVENTION

It is a primary object of this invention to provide an improved electrosurgical device having sesquipolar electrode structures incorporated therein.

It is a further object of this invention to provide a device of the above type where the ratio of the area of the active electrode to that of the return electrode is within a range appropriate for sesquipolar operation.

It is a further object of this invention to provide a device of the above type where the active and return electrodes are incorporated in a single tissue contacting structure.

It is a further object of this invention to provide a device of the above type capable of cutting and/or coagulating tissue and which may be driven by a conventional electrosurgical generator.

It is a further object of this invention to provide devices of the above type incorporating various configurations of sesquipolar electrode structures for cutting and/or coagulating.

It is a further object of this invention to provide a device of the above type which insures that the sesquipolar mode of operation is established regardless of the technique employed when using the device for cutting or coagulating.

It is a further object of this invention to provide bipolar electrosurgical devices which insure that the bipolar mode of operation is established regardless of the technique employed when using the device.

It is a further object of this invention to provide monopolar electrosurgical devices which promote uniformity of the arc established at the active electrode.

These and other advantages of the invention will become apparent from a reading of the specification and claims taken with the drawing.

DETAILED DESCRIPTION OF PREFERRED EMBODIMENT OF THE DRAWING

Figure 1:
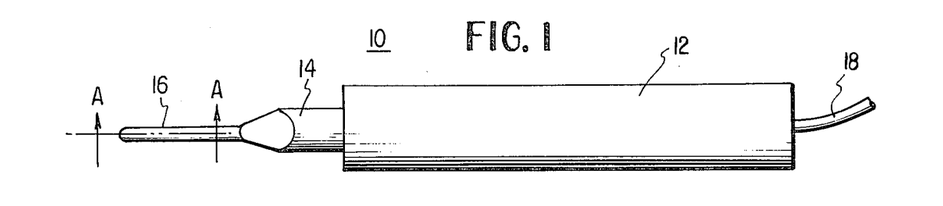
FIG. 1 is a schematic side elevation of an illustrative electrosurgical device.

Referring to FIG. 1, there is shown an electrosurgical device 10 comprising a holder 12, a blade holder 14 inserted therein, and a blade 16 supported by holder 14. As will be described hereinafter, electrodes may be supported by holder 14. Depending on the mode of operation, electrical cable 18 provides high frequency electrical energy to the electrodes of blade 16. In its broadest conception, the monopolar, bipolar or sesquipolar technology described hereinafter may be employed in electrosurgical devices other than that shown in FIG. 1 such as forceps or needles or loops.

Various embodiments of cutting blades 16 of FIG. 1 are illustrated in FIGS. 4 – 30 and 34 – 41.

Figure 3:
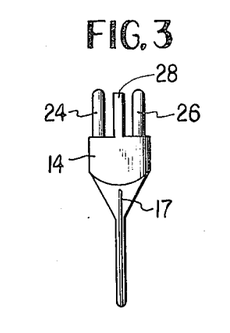
FIG. 3 is a plan view of the holder and blade of FIG. 2.
Figure 4:
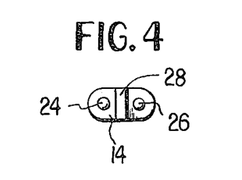
FIG. 4 is an end view of the holder of FIG. 2.
Figure 5:
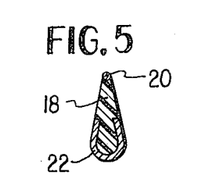
FIG. 5 is a cross-sectional view taken on line 5—5 of FIG. 6.
Figure 6:
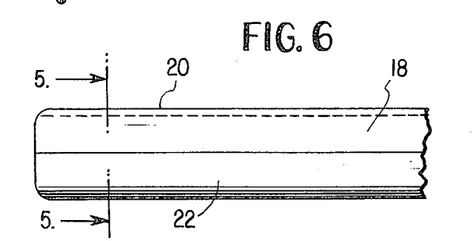
FIG. 6 is an enlarged partial side elevation view of the blade of FIG. 2.
Figure 7:
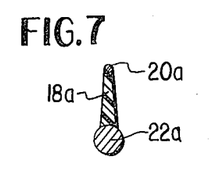
FIG. 7 is a cross-sectional view taken on line 7—7 of FIG. 8.
Figure 8:
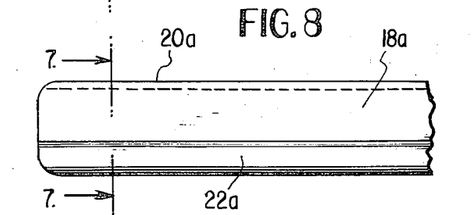
FIG. 8 is an enlarged, partial side elevation view of a further illustrative embodiment of the blade of FIG. 1.

Referring to FIGS. 2 – 6, there is shown a sesquipolar electrode configuration suitable for cutting tissue where the blade shown in the Figures corresponds to blade 16 of FIG. 1. Blade 16 is inserted in holder 14 at 17. The body 18 of blade 16 comprises an electrically insulating material such as ceramic or glass. Disposed along the forward (leftmost in FIG. 2) edge of the blade is a first or active electrode 20 which extends along the length of the blade as can be seen in FIG. 6. A second or return electrode 22 is disposed at the rear portion of the blade and is U-shaped to extend around to the sides thereof as can be seen in FIG. 5.

Figure 2:
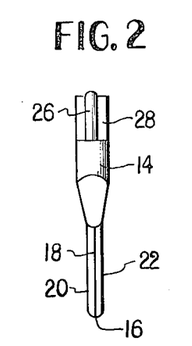
FIG. 2 is a side elevation view of an illustrative blade and holder for the device of FIG. 1 in accordance with this invention.

Disposed at the rearward end of holder 14 are electrical contacts 24 and 26. Contact 24 is connected to the active output terminal of the electrosurgical generator (not shown) while contact 26 is connected to the return output terminal thereof. The holder 14 is made of insulative material and extending therethrough are an insulated pair of wires respectively connecting contact 24 to active electrode 20 and contact 26 to return electrode 22. Holder 14 is also provided with a rearwardly extending tab 28, which facilitates insertion of the holder into a complementary female receptacle (not shown) disposed in the forward portion of holder 12, and which also provides additional insulation between contacts 24 and 26 when the holder 14 is inserted in its receptacle. Also not shown are the electrical wires extending from cable 18 through holder 12 to the receptacle for holder 14 whereby the connection between the active and return output terminals of the generator to the active and return electrodes 20 and 22 is completed. The latter electrical connection is well known in this art and as such forms no part of this invention.

Figure 9:
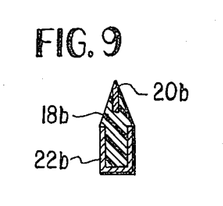
FIG. 9 is a cross-sectional view taken on line 9—9 of FIG. 10.
Figure 10:
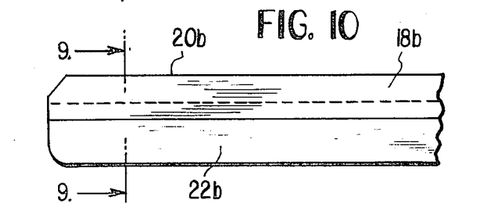
FIG. 10 is an enlarged, partial side elevation view of a further illustrative embodiment of the blade of FIG. 1.

Referring to FIGS. 7 – 20, there are shown various configurations of sesquipolar electrodes which are also suitable for cutting tissue. These blades also correspond to blade 16 of FIG. 1. Thus, in FIGS. 7 and 8 there are shown insulator 18a, active electrode 20a and return electrode 22a. In FIGS. 9 and 10 there are shown insulator 18b, active electrode 20b and return electrode 22b. In FIGS. 11 – 20, there are shown other cutting electrodes where active electrodes 20, the insulators 18 and the return electrodes 22 are distinguished from one another by an appropriate letter. The insulator may be made of such insulating materials as ceramic or glass or the like.

As will be brought out in more detail hereinafter, in all sesquipolar embodiments of this invention, the actual return electrode area which electrically connects to the tissue to be treated is greater than the corresponding area of the active electrode. In one preferred embodiment of this invention as shown in FIGS. 2 – 6, the above mentioned area of active electrode 20 is circular while the above mentioned corresponding area of return electrode 22 is U-shaped. In the preferred embodiment of FIG. 7 both of these areas are circular.

Figure 11:
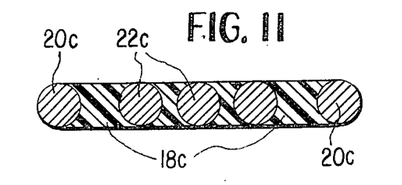
FIGS. 11 –20 are end cross-sectional views of further illustrative embodiments of the blade of FIG. 1.
Figure 12:
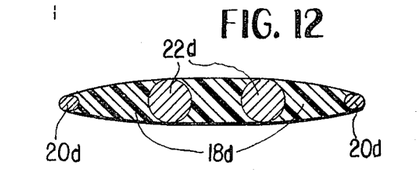
Figure 13:
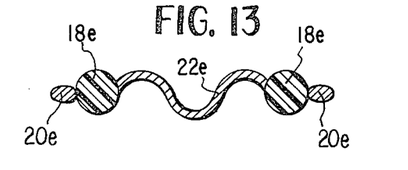
Figure 14:
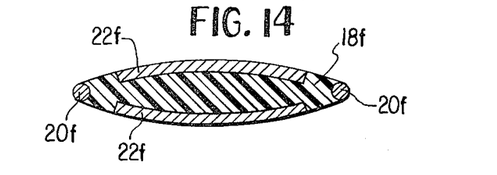
Figure 15:
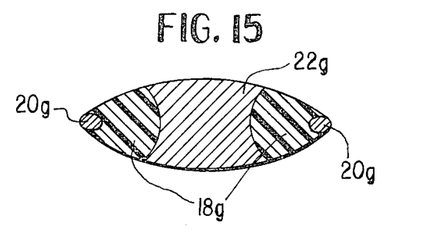
Figure 16:
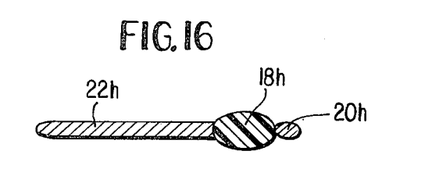
Figure 17:
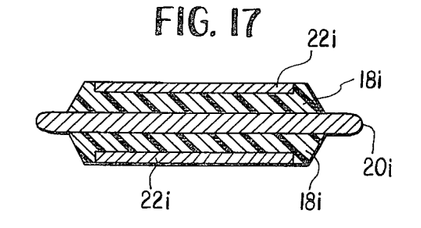
Figure 18:
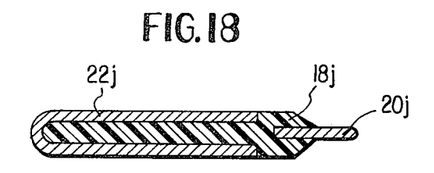
Figure 19:
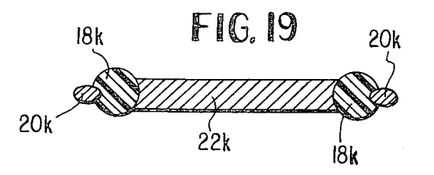
Figure 20:
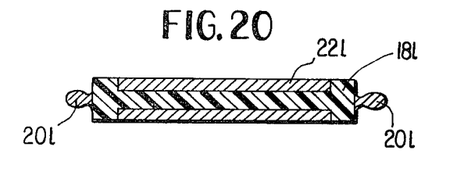

In the embodiment of FIGS. 11 – 15, and 19 – 20, at least one of either the active or the return electrode comprises a plurality of elements. In FIG. 11 the elements comprising the active and return electrodes are equal in size, there being a greater number of the return electrode elements. In FIG. 12., there are a plurality of both active and return electrode elements; however, the above mentioned area or size of the return electrode elements is greater. Because the current used in cutting is large, the heating at the return electrode may be severe - sufficient to result in thermal cautery, coagulation, or desiccation of the contacting tissues. This effect is desirable if the return electrode is within in the confines of the immediate incision, as is shown in some of the above embodiments.

Figure 21:
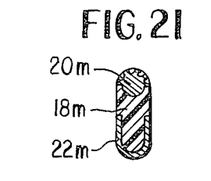
FIG. 21 is a cross-sectional view taken on line 21'21 of FIG. 22.
Figure 22:
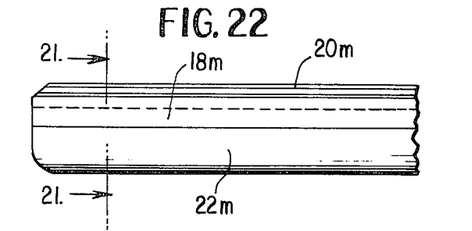
FIG. 22 is an enlarged, partial side elevation view of a further illustrative embodiment of the blade of FIG. 1.
Figure 23:
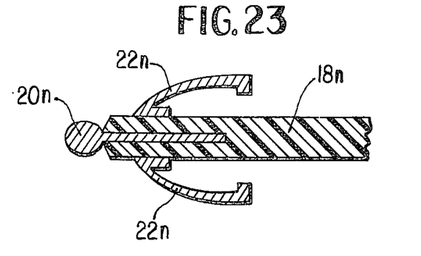
FIGS. 23 – 25 are side cross-sectional views of further illustrative embodiments of the blade of FIG. 1 taken along line A—A.
Figure 24:
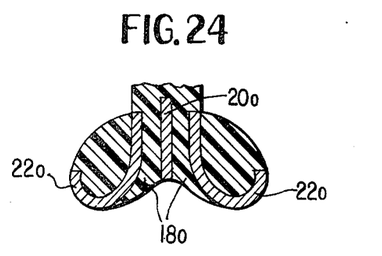
Figure 25:
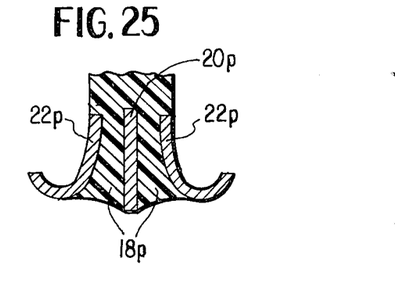
Figure 26:
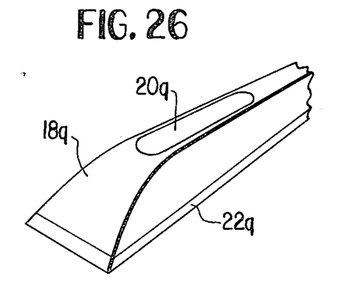
FIGS. 26 and 27 are isometric views of further illustrative embodiments of the blade of FIG. 1.
Figure 27:
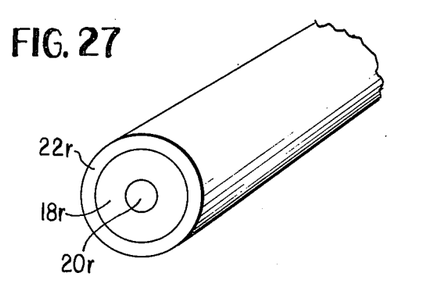
Figure 28:
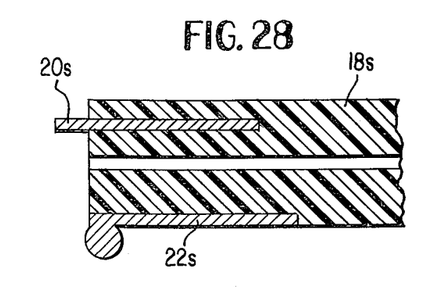
FIG. 28 is a side cross-sectional view of a further illustrative embodiment of the blade of FIG. 1 taken along line A—A.

Referring to FIGS. 21 and 22, there is shown an embodiment of a coagulating electrode comprising insulator 18 m, active electrode 20 m and return electrode 22 m. As can be appreciated by comparing the leading edge (where the active electrode is disposed) of the cogulating electrode of FIG. 21 with the leading edge of the cutting electrode of FIG. 5, the leading edge of the coagulating electrode is more blunt than the leading edge of cutting electrode. Further, as is well known, the intensity of the coagulation current applied to a coagulating electrode is less than that of cutting current applied to a cutting electrode. Further, the wave shape of the coagulating current differs from that of the cutting current. As such, these factors are well known and do not form a part of this invention.

Other configurations of coagulating electrodes are shown in FIGS. 23 – 28 where the insulator 18, active electrode 20, and return electrode 22 are also distinguished from one another by an appropriate letter. Since the current at the return electrode may be quite small for coagulation electrodes, it is possible to have the return electrode outside of the immediate coagulation field, as can be appreciated in FIGS. 23, 25 and 28.

It should be noted that in the embodiment of FIGS. 1–20, 26 and 28, the entirety (that is, all elements) of the return electrode is asymmetrically disposed with respect to one element of the active electrode. Thus, for example, in FIG. 11, all three return electrode elements 22c are asymmetric with respect to the active electrode element 20c disposed at the left side of the blade. This is in contradistinction to the embodiments of FIGS. 23–25 and 27 where, for example, in FIG. 27 the return electrode 22r is symmetrically disposed with respect to the one element comprising the active electrode 20r. Hence, the embodiments of FIG. 1–20, 26 and 28 are particularly suitable for cutting due to the above-discussed asymmetric arrangement.

Figure 31:
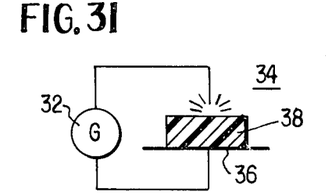
FIGS. 31 – 33 are schematic diagrams of circuitry for respectively illustrating the monopolar, bipolar, and sesquipolar modes of operation.
Figure 32:
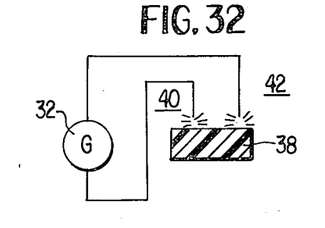
Figure 33:
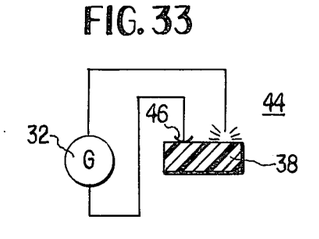

FIGS. 31 – 33 respectively illustrate the monopolar, bipolar and sesquipolar modes of operation of an electrosurgical device. In FIG. 31 there is shown an electrosurgical generator 32 with an active electrode indicated at 34 and a large area return electrode 36. The electrodes are applied across tissue 38 and a radio frequency arc to the tissue is generated at active electrode 34 and is so indicated in FIG. 31. This arc dissipates great energy at the tissue interface, exploding cells in the cutting mode of operation of dehydrating and fusing to a greater depth in the coagulation mode. Which mode occurs is a function of signal intensity, wave form and technique as will be described in more detail hereinafter. The mechanisms within these radio frequency arcs are not completely understood; however, there is no intention to be bound by a particular theory of operation.

Referring to FIG. 32, there is illustrated the bipolar mode of operation where there are two active electrodes indicated at 40 and 42. There is no ohmic contact, as is the case at return electrode 36 of FIG. 31. Thus, the "return" electrode 40 is identical to the "active" electrode 42 in the bipolar mode of operation.

Referring to FIG. 33, there is illustrated the sesquipolar mode of operation where a radio frequency arc is established at active electrode 44 while an ohmic connection is established at return electrode 46. Thus, for sesquipolar electrosurgery, an intermediate situation applies. In bipolar electrosurgery, both electrodes should behave identically — arcwise for needles, ohmically for forcep tips. It is difficult to establish identical states at both electrodes with a bipolar device, as has been discussed hereinbefore. The sesquipolar electrode device of this invention operates in a mode, as shown in FIG. 33, where identical behavior at both electrodes is not necessary. However, some of the sesquipolar electrode embodiments discussed hereinbefore tend to be dependent on the technique employed in using them as to whether the sesquipolar mode is established.

Before discussing this dependency on technique further, a proposed theory of operation will be discussed for the sesquipolar mode of operation, assuming that both the active and return electrodes have been pressed to the tissue to be treated prior to the energization thereof with high frequency electrical current.

The exact nature of the active electrode/body interaction is not known for certain — nor is that of the return electrode/body mechanism. It is also likely that the nature of these mechanisms may vary to some degree with the particular technique employed and the current level. However, very elementary measurements show that the voltage difference between the active electrode and the body is very great (hundreds of volts), while that between the return electrode and the body is very small (a few volts) during the flow of significant electrosurgical currents. This is perhaps analogous to arc welding, in that the arc effect is very different from the simple conduction at the return electrode attachment site. "Arc" is perhaps too specific a term, in that it implies considerable mechanism restraints which are not known to specifically apply to the present invention. This term, however, is used to mean whatever process beyond ohmic heating causes power to be dissipated at the active electrode site.

A possible mechanism for cutting via arc formation at the active electrode which is very small relative to the return electrode, and which is pressed against the flesh or tissue, is as follows. Current (I) flowing through the impedance (Z) of the interface between the electrode and the flesh dissipates power. Power, $(W) = I^2Z$, heats ohmically the flesh at the interface. When the heat is sufficiently intense, vaporization occurs, high voltage appears across the vapor barrier, arc breakdown occurs in the vapor, and the electrode is held away from the flesh by the issuing vapors, perpetuating the arc. With high currents flowing across the voltage drop of the arc, great power is dissipated. The arc is most intense at the leading edge of the electrode (shape factor), vaporizing the flesh away in this direction preferentially. This permits the electrode to move through the flesh easily in this direction. Those elements of the flesh that are not vaporized by the arc are touched physically by the electrode, establishing again $I^2Z$ heating to burn away these elements.

At the return electrode interface the $I^2Z$ heating will also occur, but due to the larger area, the current density is so low that the body is able to dissipate the heat generated without appreciable temperature rise. No vaporization nor cell damage occurs, and no arc is created. Because there is no mechanism present here to change the impedance of the interface nor create a vapor barrier with high potentials across it, there is no arc formation, and thus very little power is dissipated at this interface. Thus the mechanisms of these electrodes are quite different under classical monopolar conditions.

If the size of the return electrode is sufficiently small, it can be placed on the same probe, which holds the active electrode, as is shown in various Figures of the Drawing. The heating at the return electrode interface may be considerable, but most not be readily capable of arc generation. This differs from the bipolar condition primarily in that no arc can occur at the return electrode due to its larger size and/or other factors.

The size relationships between monopolar, bipolar and sesquipolar can be defined as follows:

R = Return electrode area/Active electrode area where the area of each electrode is that area of the electrode which provides an electrical connection to the tissue to be treated where the connection might be direct (ohmic) or arcwise.

The value of the ratio R for monopolar electrosurgery ranges from about 400 to over one million. For the bipolar case the value of R is necessarily very close to unity. The value of R for sesquipolar operation approximately falls between about 2 and 200. The smaller the ratio, the easier the task of designing practical electrodes to utilize the effect. Ratios greater than about 50 often require size and convenience compromises. Electrodes with ratios less than about 3 tend to lapse into occasional bipolar operation, giving inconsistent operation. Ratios from 3 to about 50 therefore appear most practical for sesquipolar operation.

To summarize, characteristics of the sesquipolar mode of operation are as follows: (1) arc or other large voltage drop processes are active at one electrode only (as in monopolar, but unlike bipolar); (2) both electrodes may be in the operation site (as in bipolar, but unlike monopolar); (3) the return electrode may be active, but short of arc formation (unlike either monopolar or bipolar modes); and (4) R equals values of 2 – 200.

Thus, it can be seen that an arc is effectively established at the active electrode while an ohmic connection is established at the return electrode when both electrodes have contacted the tissue to be treated prior to the application of electrical power thereto. If power has been applied to the electrodes prior to the contacting of the tissue, the mode of operation is somewhat dependent on the order that the electrodes are applied to the tissue — that is, the established mode is somewhat dependent on the technique employed when using the instrument. Thus, if both electrodes contact the tissue simultaneously, the sesquipolar mode is discussed above will be established. However, it is of course difficult to insure simultaneous contact of the tissue by both electrodes.

If the return electrode contacts the tissue first, the desired arc will naturally develop at the active electrode since it will be slightly spaced from the tissue when an ohmic connection has been established at the return electrode. Hence, for certain of the sesquipolar electrode embodiments described hereinbefore, desired technique would require that the operator contact the tissue with the return electrode prior to contact thereof by the active electrode, assuming that the device has been previously energized. However, even if this isn't done, the sesquipolar mode of operation will normally eventually be established. Thus, if the active electrode contacts the tissue first, an arc will often develop at the larger, return electrode. This cannot be maintained unless extremely improbable measures are taken by the operator. Thus, a brief bipolar transition state occurs shortly thereafter followed by the eventual establishment of the desired mode of sesquipolar operation. It has been observed that a substantial amount of cutting can occur with the return electrode until the sesquipolar mode of operation is eventually established, which quickly occurs, as stated above.

The probability of establishing the sesquipolar mode of operation is substantially improved with the particular arrangements of active and return electrodes in the sesquipolar electrode embodiments described hereinbefore. Also, as stated above, the probability of establishing this mode for certain electrode arrangements can be enhanced by use of proper technique. In particular, establishment of the sesquipolar mode of operation basically depends on the following factors: (1) area ratio of return electrode to active electrode (the area of the return electrode must be greater than that of the active electrode), (2) the order of electrode contact (the return electrode should contact the tissue to be treated substantially more than the active electrode when the instrument is first placed in contact with the tissue), and (3) the relative contact pressure (the pressure on the return electrode should be greater than that on the active electrode). Since for certain sesquipolar electrode embodiments, the second and third factors mentioned above could override the first defining factor, certain embodiments tend to be more advantageous since they are less depedent on technique.

Figure 29:
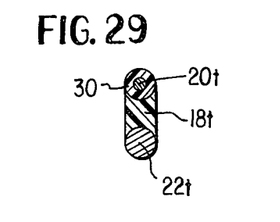
FIG. 29 is a cross-sectional view taken on line 29—29 of FIG. 30.
Figure 30:
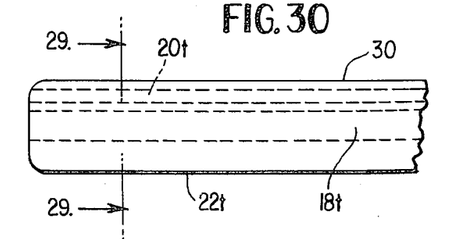
FIG. 30 is an enlarged, partial side elevation view of a further illustrative embodiment of the blade of FIG. 1.

In FIGS. 29 and 30 there is shown an embodiment which insures the establishment of an arc at the active electrode regardless of the technique employed in using the instrument, assuming the instrument has been previously energized. In particular, there is shown a porous, insulative covering 30 for active electrode 20t. Covering 30 insures the establishment of an arc at the active electrode because: (1) the porous medium of covering 30 reduces the effective electrode area of active electrode 20t to a very small fraction of its uncovered or unguarded value (thus, the ratio of the area of the return electrode to that of the active electrode is substantially increased), (2) the covering 30 prevents direct contact between the tissue and the active electrode (thus, the return electrode must contact the tissue first), and (3) further, since the covering 30 prevents direct contact between the tissue and the active electrode, the return electrode must necessarily exert greater pressure against the tissue. Basically, the covering 30 necessarily introduces a gap between the tissue and the active electrode and thus if current is to flow, it must necessarily flow as an arc as it jumps the gap.

The porous insulative coating 30 may comprise a particulate coating of alumina or glass or the like where the coefficient of expansion of the coating is preferably substantially matched to that of the electrodes. The thickness of the coating is typically 5 – 10 mils assuming that the pores of the coating are small. The purpose of the pores is to permit arc formation to occur between the tissue and the active electrode. The pores must not be so large that tissue can extrude through the pores when the device is pressed against it. Thus, direct contact between the tissue and the active electrode must be avoided if an arc is to be guaranteed. If the spacing between the tissue and electrode is sufficient, it is possible to eliminate the need for the porous coating. Thus, as will be described hereinafter with respect to FIGS. 38 – 41, the active electrode may be recessed in such a manner as to effectively "guard" it as described above while at the same time preventing direct contact between the electrode and the tissue as the device is being pressed against the tissue.

Thus, broadly speaking, the establishment of an arc at the active electrode is ensured by any means which forces a separation between the active electrode and the tissue to be treated where this means may comprise the porous covering 30 or the recessing of active electrode 20 as discussed above. The use of the guarded electrode technology has been found to be particularly advantageous when applied to coagulation devices.

Figure 34:
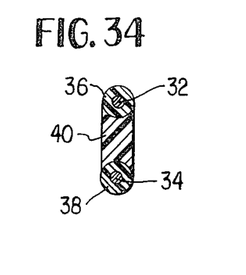
FIG. 34 is a cross-sectional view taken on line 34—34 of FIG. 35.
Figure 35:
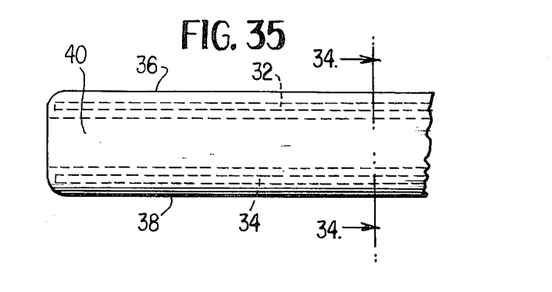
FIG. 35 is an enlarged partial side elevation view of a further illustrative embodiment of the blade of FIG. 1.

The covered or guarded electrode technology is also applicable to bipolar or monopolar devices. Thus, with bipolar devices (where the area of the respective electrodes is equal), the use of guarded or covered electrodes will insure that arcing occurs at both electrodes. If the electrodes are uncovered, as is conventionally the case, the establishment of the bipolar mode of operation see FIG. 32 is dependent on technique, as described above, Thus, if one of the electrodes contacts the tissue prior to contact by the other or is held with greater pressure against the tissue than the other, the sesquipolar mode of operation tends to be established. This can be avoided by covering both electrodes. Thus, the use of covered or guarded electrodes tends to insure that equivalent conduction states are established at both electrodes. An illustrative bipolar tool is schematically indicated in FIG. 34 where the blade only of the tool is shown, the blade including electrodes 32 and 34 respectively covered or guarded by porous, insulative coverings 36 and 38 at opposite ends of insulative body 40. Coverings 36 and 38 and insulative body 40 can be made of the same materials mentioned hereinbefore for covering 30 and insulative body 18, respectively.

Figure 36:
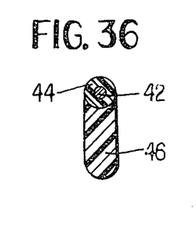
FIG. 36 is a cross-sectional view taken on line 36—36 of FIG. 37.
Figure 37:
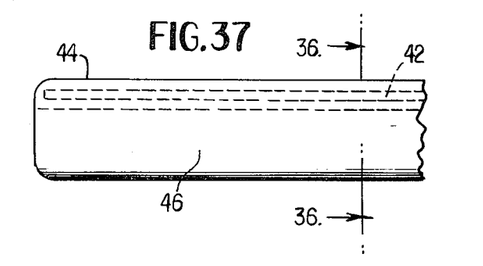
FIG. 37 is an enlarged, partial side elevation view of an illustrative further embodiment of the blade of FIG. 1.
Figure 38:
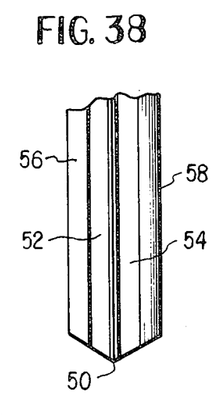
FIG. 38 is a forward end view of a further illustrative embodiment of the blade of FIG. 1.

As stated hereinbefore, it is desirable with monopolar devices to generate a uniform arc at the active electrode. The provision of a guard or covering for the active electrode may substantially improve the uniformity of this arc. Hence, the application of the guarded electrode technique to monopolar electrode devices is also apparently advantageous. Referring to FIGS. 36 and 37 there is shown a monopolar electrosurgical tool, and in particular, a blade for use therein comprising an active electrode 42, a covering 44 and an insulative body 46. The materials comprising porous, insulative covering 44 and insulative body 46 can be the same as those mentioned hereinbefore for covering 30 and body 18 respectively. The return electrode is not shown in FIGS. 36 and 37 since it would be substantially removed from the surgical site in this monopolar embodiment.

Figure 39:
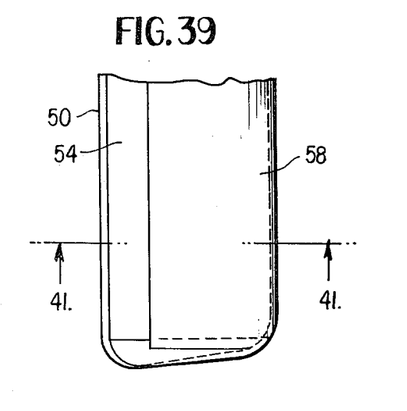
FIG. 39 is a side elevation of the blade of FIG. 38.
Figure 40:
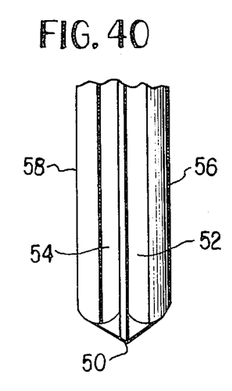
FIG. 40 is a rearward end view of the blade of FIG. 38.
Figure 41:
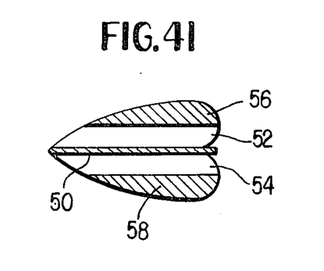
FIG. 41 is a cross-sectional view taken on line 41—41 of FIG. 39.

Referring now to FIGS. 38 – 41, there are shown various views of an electrosurgical sesquipolar device capable of operating in either the cutting or coagulation mode where operation in the coagulation mode effectively utilizes the guarded electrode technique described hereinbefore. In the Figures there is shown an active electrode 50 interposed between two insulative layers 52 and 54, which in turn are disposed between outer, return electrodes 56 and 58 as can best be seen in FIG. 41. The forward side of the blade (leftmost in FIGS. 39 and 41) is utilized for cutting while the rearward side is utilized for coagulation. As can be seen in FIG. 39, the lower edge of the active electrode 50 is inclined upwardly from the forward to the rear portion of the blade. Also, the lower edges of insulating slabs or layers 52 and 54 are inclined upwardly from the forward to the rear portion of the blade. However, the upward incline of active electrode 50 is greater than that of insulating layers 52 and 54 and thus on the coagulation side of the blade, the active electrode 50 is recessed between the insulative layers 52 and 54. Thus, when the coagulation side of the blade is pressed against the tissue to be coagulated, the return electrodes 56 and 58 (both of which would be connected to the return output terminal of the generator) necessarily contact the tissue first thus insuring an ohmic contact thereat and the generation of a coagulation arc at active electrodes 50. That is, since active electrode 50 is recessed at the coagulation side between the insulative layers, a gap is necessarily established between the active electrode and the tissue so that arcing will necessarily occur therebetween when the coagulation side of the blade is pressed against the tissue.

When the cutting side of the combination blade is pressed against the tissue, there will be a tendency for the active electrode to contact the tissue first. If the blade is energized prior to tissue contact, as discussed hereinbefore, a reverse sesquipolar mode of operation may temporarily be initiated whereby a cutting arc would be briefly established at the return electrodes 56 and 58. However, this would quickly change over to the normal sesquipolar mode of operation as the tool briefly passed through a bipolar state, as has been described hereinbefore. Thus, the embodiment of FIGS. 38 – 41 is particularly advantageously in that there is incorporated in a single blade the capability effecting either cutting or coagulation operations. Such a blade would necessarily have wide utility.

What is claimed is:

1. An electrosurgical device adapted for connection to an electrical generator having active and return output terminals, said device being used to cut, coagulate, or otherwise treat human tissue or the like, said device comprising:
an insulative electrode support means;

an active electrode comprising at least one conductive element responsive to said active output terminal and a return electrode comprising at least one conductive element responsive to said return output terminal, said electrodes being supported by said electrode support means, the entirety of said return electrode being asymmetrically disposed with respect to said one element of said active electrode, said active and return electrodes being rigidly supported a fixed distance apart by said electrode support means, both said electrodes being adapted for electrical connection to said tissue, the ratio of the return electrode area adapted to electrically connect to said tissue to the active electrode area adapted to electrically connect to said tissue being in the range of approximately 2 to 200; and means for connecting said active electrode to said active output terminal and said return electrode to said return output terminal whereby said electrosurgical device can be used for cutting of said tissue due to said entirety of said return electrode being asymmetrically disposed with respect to said one active electrode element.

2. An electrosurgical device as in claim 1 where said area range is approximately 3 to 50.

3. An electrosurgical device as in claim 1 where said electrode support means includes a handle and a single tissue contacting structure disposed at one end of said handle and supporting said electrodes.

4. An electrosurgical device as in claim 3 where said active and return electrodes each comprise a single element, the size of said return electrode element being greater than that of said active electrode element.

5. An electrosurgical device as in claim 4 where said active and return electrode areas are both circular and are disposed at opposite sides of said structure.

6. An electrosurgical device as in claim 4 where said active electrode area is circular and disposed at one side of said structure and said return electrode area is U-shaped and disposed at the side of said structure opposite said one side.

7. An electrosurgical device as in claim 3 where at least one of said active and return electrodes comprises a plurality of elements.

8. An electrosurgical device as in claim 7 where both said active and return electrodes comprise a plurality of elements of equal size, the number of return electrode elements being greater than that of the active electrode elements.

* * * * *